United States Patent [19]

Collier et al.

[11] Patent Number: 5,578,201

[45] Date of Patent: Nov. 26, 1996

[54] APPARATUS FOR MIXING LIQUIDS USED IN COUNTERCURRENT MULTIPHASE LIQUID SEPARATION

[75] Inventors: Charles F. Collier; Brian A. Deane, both of Wilmington, Del.; William E. Feathers, Cochranville, Pa.; Robert A. King, Hockessin; Alexander D. Kopatsis, Wilmington, both of Del.; Thomas P. Ladisch, Alburtis, Pa.; Peter M. Mrozinski, Hockessin; Norman P. Pih, Newark, both of Del.

[73] Assignee: E. I. du Pont de Nemours and Company, Wilmington, Del.

[21] Appl. No.: 451,353

[22] Filed: May 26, 1995

Related U.S. Application Data

[63] Continuation of Ser. No. 99,891, Jul. 30, 1993, abandoned.

[51] Int. Cl.⁶ .................................................. B01D 11/04
[52] U.S. Cl. .................... 210/142; 210/511; 366/132; 366/241; 366/273; 422/101; 422/103; 422/255; 422/258
[58] Field of Search ................................. 210/511, 634, 210/143, 141, 142; 422/100–104, 116, 255, 269, 258, 259; 435/177, 178, 180; 366/131, 132, 273, 241

[56] References Cited

U.S. PATENT DOCUMENTS

| | | | |
|---|---|---|---|
| 3,650,306 | 3/1972 | Lancaster | 141/238 |
| 3,752,651 | 8/1973 | Bush . | |
| 3,789,670 | 2/1974 | Rosenwald | 366/273 |
| 3,882,716 | 5/1975 | Beiman | 73/61.4 |
| 4,477,578 | 10/1984 | Miles et al. | 436/820 |
| 4,749,658 | 6/1988 | Jaekel et al. | 436/180 |
| 4,859,336 | 8/1989 | Savas et al. | 210/416.1 |
| 4,889,692 | 12/1989 | Holtzman | 422/102 |
| 4,897,193 | 1/1990 | Cais | 210/359 |
| 5,147,323 | 9/1992 | Haber et al. | 604/191 |
| 5,352,036 | 10/1994 | Haber et al. | 366/273 |

FOREIGN PATENT DOCUMENTS

| | | | |
|---|---|---|---|
| 2030110 | 4/1980 | United Kingdom . | |
| WO90/05768 | 5/1990 | WIPO | 210/511 |

OTHER PUBLICATIONS

Albertsson, P., *Partition of Cell Particles and Macromolecules,* (3rd ed.), John Wiley & Sons, NY, pp. 126–131, Date Unknown.

P. Albertsson, "Partition of Cell Particles and Macromolecules", pp. 126–131 (3rd Edition)., 1986.

*Primary Examiner*—Joseph W. Drodge

[57] ABSTRACT

A reusable apparatus for multiphase, multistage countercurrent liquid separation is presented. The apparatus is particular useful in progressive multistage separation of target microorganisms from background organisms and materials with precise transfer, air exclusion, homogeneous mixing, isolation from the ambient atmosphere, in the absence of valves and at ow cost. The structure has at least one chamber in which a piston-like sliding bottom is sealingly moved or braked and includes internal structure for mixing, preferably a magnetic-stainless steel ball which can be reciprocated from the outside to mix the liquid contents. Motion of the bottom is limited by stops. A number of ways to actuate the apparatus are taught.

45 Claims, 11 Drawing Sheets

APPARATUS FOR MIXING LIQUIDS USED IN COUNTERCURRENT MULTIPHASE LIQUID SEPARATION

This is a continuation of application Ser. No. 08/099,891 filed Jul. 30, 1993, now abandoned.

BACKGROUND OF THE INVENTION

The present invention relates to an apparatus for multiphase aqueous separation and more specifically to an apparatus for multistage, countercurrent (sequential) two-phase separation, and is particularly useful for partitioning specific target microorganisms from background material and organisms.

Traditionally, multiphase liquid separation is a labor intensive, hand-operated, wet-lab procedure carried out in laboratory glassware or the like. The extraction procedures are routinely adapted and utilized to extract and separate various reagents, compounds, particles, or other desired samples from their background liquids. The extraction liquids may be any combination of liquids which due to their thermodynamic or solubility properties are able to separate into phases. Typically, extraction by these techniques utilizes two phases for separation, however, a particular extraction protocol could be designed to utilize three or even more phases. Further, the procedure is routinely practiced repetitively, wherein a portion or all of a phase containing the desired sample from one stage is added as the sample to a next stage containing fresh extraction liquids. Thus, the procedure generally can be practiced as multiphase, utilizing two or more phases; and as multistage, wherein the procedure is repeated to enhance the purity of the extracted samples.

In the present system, Applicants have embodied the apparatus of the invention to demonstrate the extraction of target microbial cells from background cells and other materials. A two phase, three stage system is demonstrated utilizing the aqueous polymer phases of polyethylene glycol polyethylene glycol (PEG) and dextran (DEX), which are known in the art to have wide application for the separation of biological materials. Advantages of the disclosed apparatus in this context include increased handling efficiency, reliability, and safety to laboratory workers, especially when contact with the phase liquids or microbial samples is potentially harmful.

A microbiological practice based upon PEG and DEX is described in Walter, H., et al., "Partitioning in Aqueous Two-Phase Systems" (Academic Press, 1985) and Albertsson, "Partitioning of Cell Particles and Macromolecules", 3rd edition (Wiley, 1986). The latter publication describes apparatus for countercurrent distribution of organic matter in phase separation. This apparatus is characterized by complexity and high cost, and requires cleaning between runs to insure absence of contamination.

Strom, in International Application WO 90/05768, describes large-scale industrial apparatus for two-phase polymeric separation of lubricating agents from bacterial contaminants. Only a single-separation, bottom phase accumulation of bacterially contaminated solution is described.

SUMMARY OF THE INVENTION

The invention is a consumable apparatus for aqueous, two-phase, progressive multi-stage separation of target microorganisms from background organisms and materials. The consumable apparatus provides: 1) accurate and precise transfer of the liquid two-phase medium progressively from stage to stage; 2) liquid filling with exclusion of air; 3) means for adequate, homogeneous mixing; 4) valveless construction; 5) isolation of the liquid medium and contents from the ambient atmosphere; and 6) low cost permitting disposal after use. Preferred apparatus for housing and processing of the consumable are part of the invention. Although Applicants herein have named the separating apparatus of the invention as "consumable", referring to a major advantage of the device, obviously the device could alternatively be reused in some circumstances, and the necessity of disposing the device after each single use is not inherent in its design.

The consumable incorporates four closed chambers in a body which, preferably, is made from an injection molded plastic. Inside each chamber is a sliding bottom (piston) made of elastomeric material. These create a fluid-tight seal in each chamber and can slide up/down to change the chamber's volume. At the top of each chamber are two ports (through holes in the top of the body). Also at the top of the body; a film is laid down and sealed appropriately to interconnect the first and second chambers, the second and third chambers, and the third and fourth chambers, respectively. The first chamber has a luer fitting, covered with a cap closure, for initial filling with the sample fluid. Chamber #4 has an access port, covered with a removable/replaceable plastic plug, for discharge of the separated material.

A 400 series (ferromagnetic) stainless steel ball bearing is inside each of chambers 1, 2, & 3. Fluid is mixed by magnets in proximity to the balls driven by a reciprocating mechanism which runs the magnets, and the balls, up and down repeatedly to create a homogeneous emulsion.

The first three chambers carry a charge of a selected aqueous, two-phase medium. The first chamber is initially charged with 4 mL of medium which places the sliding bottom in that chamber at a 1 mL volume location below a step which prevents any movement (upwardly) beyond the 3 mL volume level. The next two chambers are initially filled with 3 mL of two-phase medium, each with their respective sliding bottoms against steps. The fourth chamber is empty with the sliding bottom at its uppermost position there being no step in that chamber.

To the first chamber 1 mL of sample fluid is added by inoculation through the luer fitting, bringing the total volume in that chamber to 5 mL. The sliding bottom in that chamber is forced down to accommodate the fluid volume. During filling, an isolation cap, snapped onto the assembly, exerts a sealing pressure on a sealing film or membrane that covers the transfer passages to prevent carry-over to the downstream chambers. After the inoculation, the isolation cap is removed. The contents of the first chamber then are mixed. Preferably, the consumable is placed in a mixing instrument or a combined mixing/actuating instrument to accomplish mixing. Then the consumable is left standing for an appropriate amount of time until separation of the medium into phases takes place. Then 2 mL of the upper or bottom phase, whichever is appropriate, is transferred from the first to the second chamber. Then after mixing and standing, 2 mL from the second chamber is transferred to the third chamber. Carryover in these transfers is prevented by braking the sliding bottoms in the non-involved chambers.

Transfers are accomplished in the actuating instrument by using a series of vertical actuators (translatable rods) that push the sliding bottoms up. First, the consumable is positioned above these actuators. Next, the appropriate, downstream, actuators are driven up to fix or anchor the two sliding bottoms which are not to be moved. Then, the appropriate actuator is slowly driven up to move the sliding bottom against a step in the chamber, thereby transferring fluid to the adjacent chamber. In our preferred apparatus, we transfer 2 mL. The sliding bottom in the filling chamber, which is not anchored, moves down to accommodate the volume of fluid received. Obviously, although the present apparatus is embodied using a total of 5 mLs in each chamber, the apparatus could easily be designed to accommodate other volume and transfer volume ranges.

The consumable optionally is received as a kit in a sterile pouch with chambers preloaded with a two-phase medium selected for "top" or "bottom" isolation. In the filling of the aqueous medium, an inverted consumable is loaded with a measured charge of liquid and then the sliding bottoms, fitted with removeable means to allow air to bleed past the bottom, are inserted. Selection of the separation medium and preferred volumes and concentrations will be specific to the target microorganism or other sample type to be separated, often PEG and dextran will be the medium conveniently of choice. Target organisms that require both "top" and "bottom" systems have a double pouch containing a "top" and a "bottom" consumable. These differ in the two-phase media with which they are filled and may be keyed to fit into the correct actuating device so that the consumable is properly oriented vertically during processing.

Optionally, also in the pouch is a plastic syringe tip for inoculation of the the proper diameter to fit neatly on a syringe luer tip permitting the operator to withdraw material from the sample container containing the target bacteria.

DETAILED DESCRIPTION OF THE PREFERRED EMBODIMENT

Figure 1:
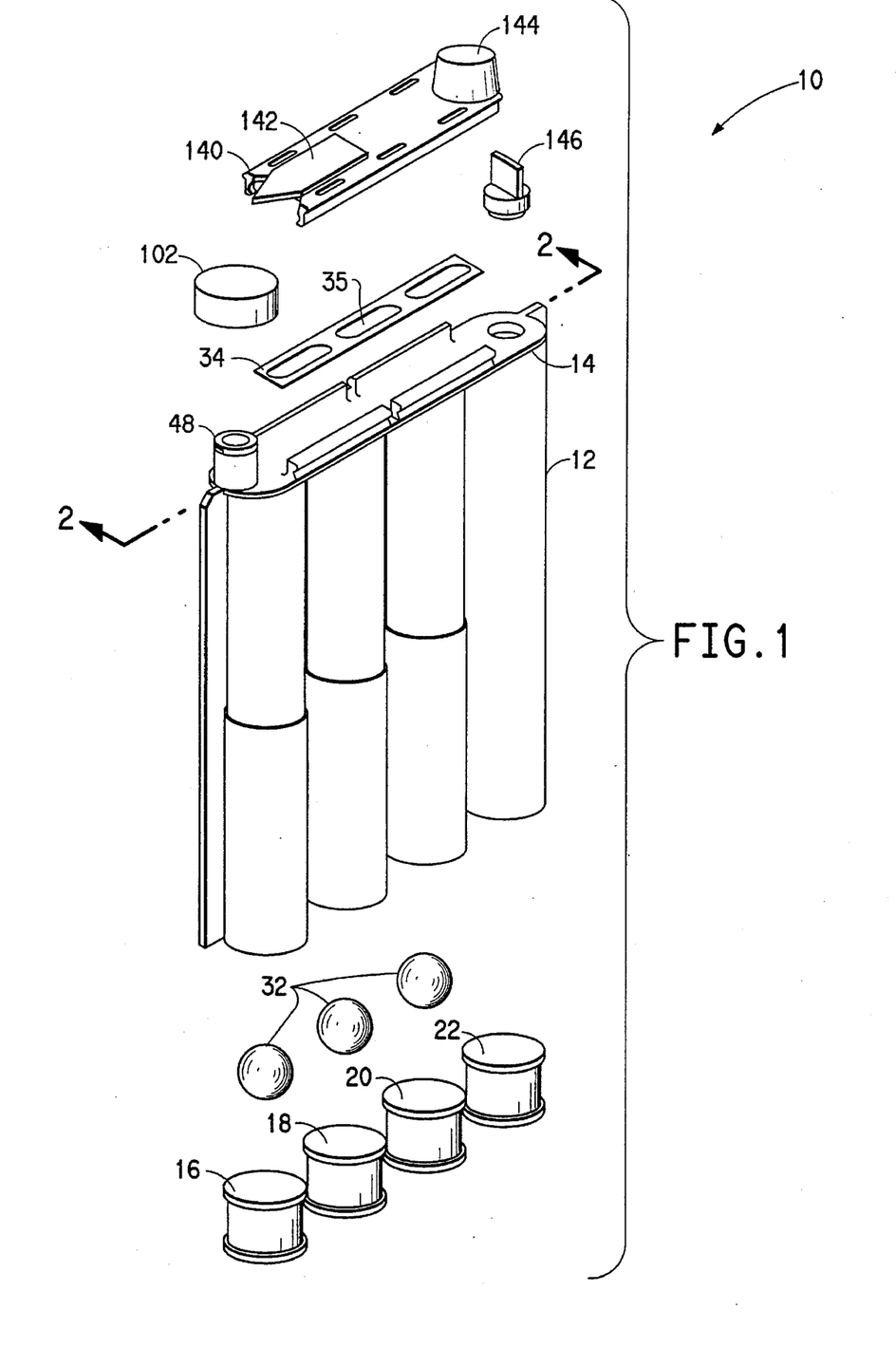
FIG. 1 is a perspective exploded view of the consumable apparatus according to the invention.
Figure 2:
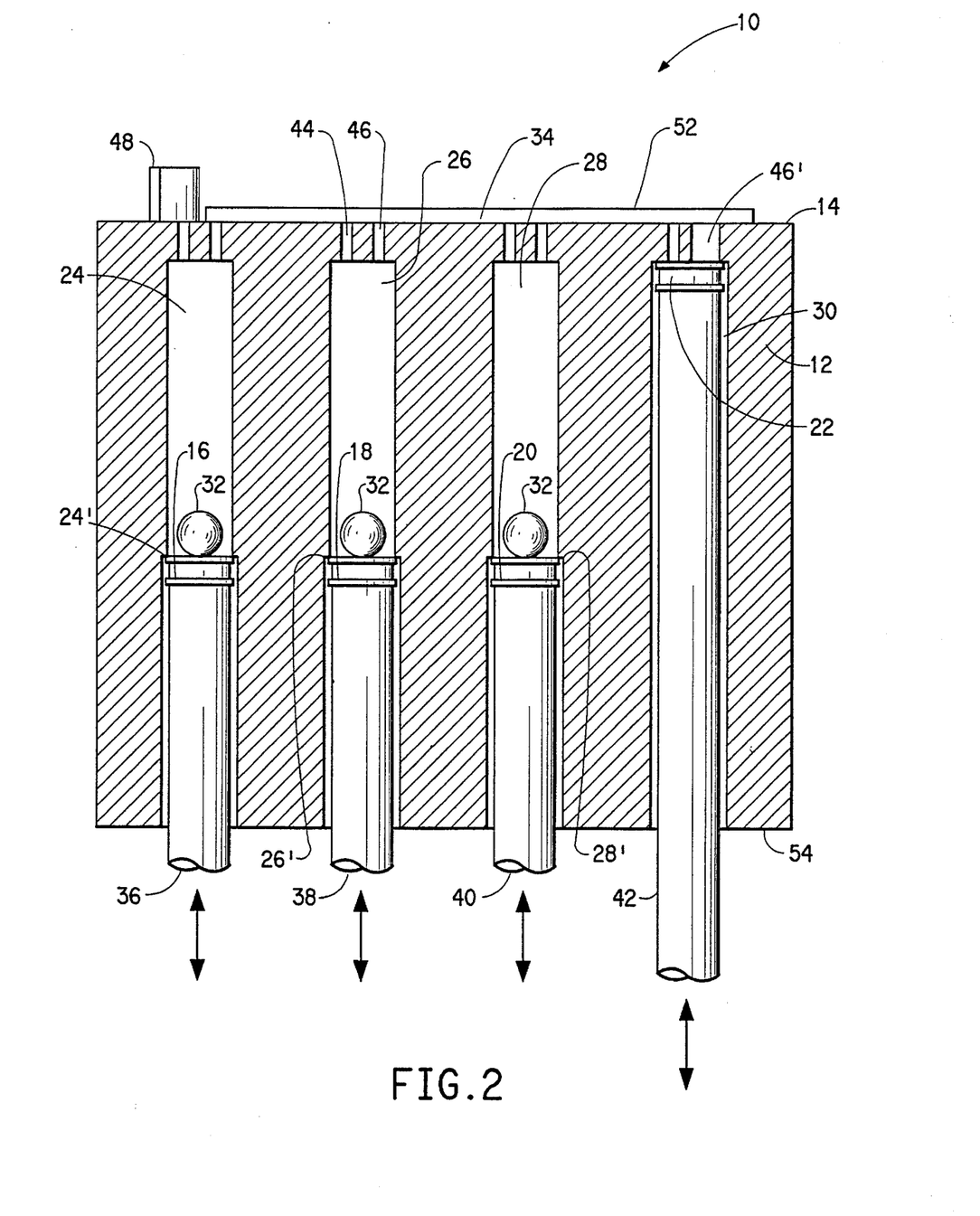
FIG. 2 is a schematic cross-section of the consumable apparatus taken on the line 2—2 of FIG. 1.
Figure 3:
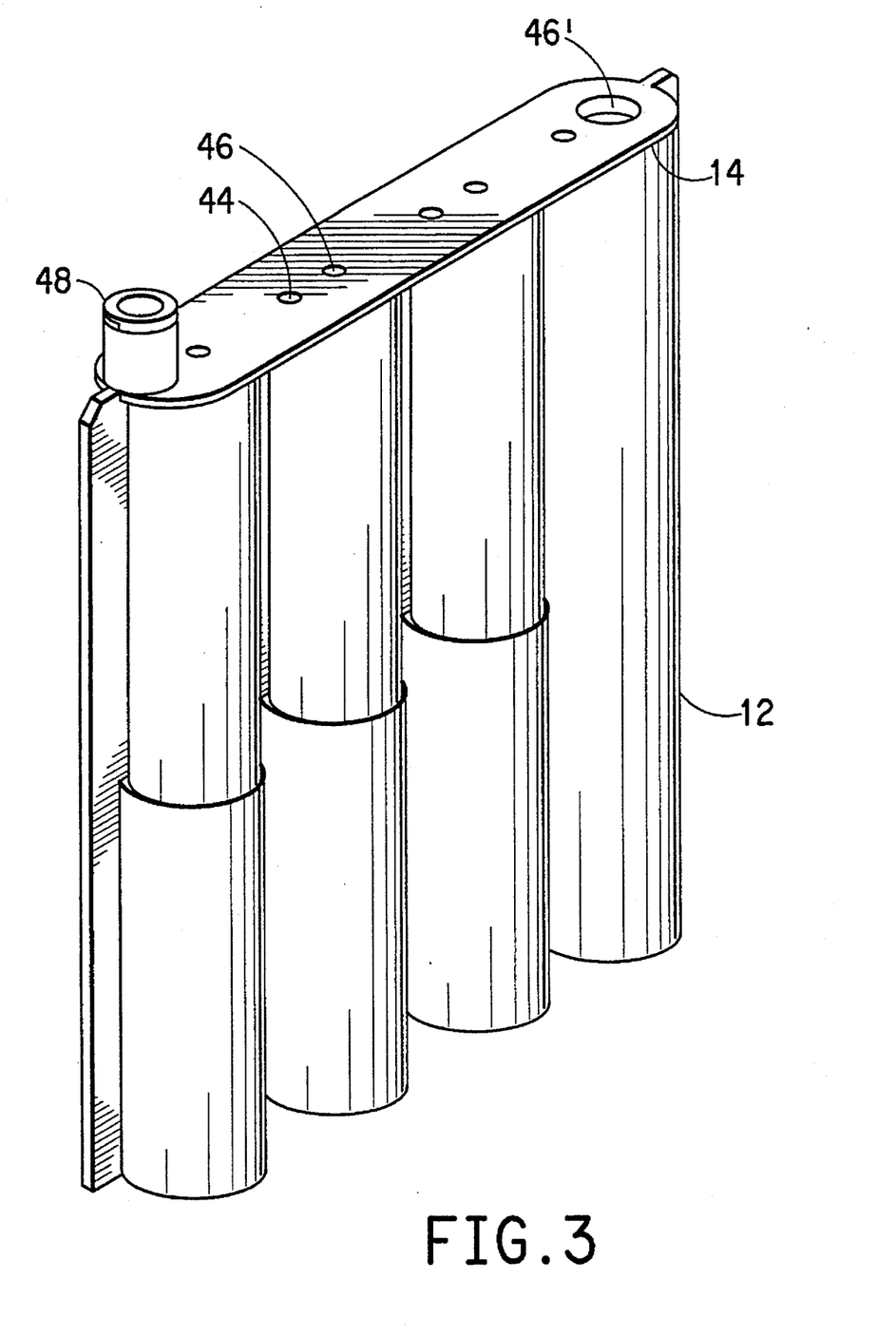
FIG. 3 is a perspective view of the consumable apparatus without the membrane seal.
Figure 6:
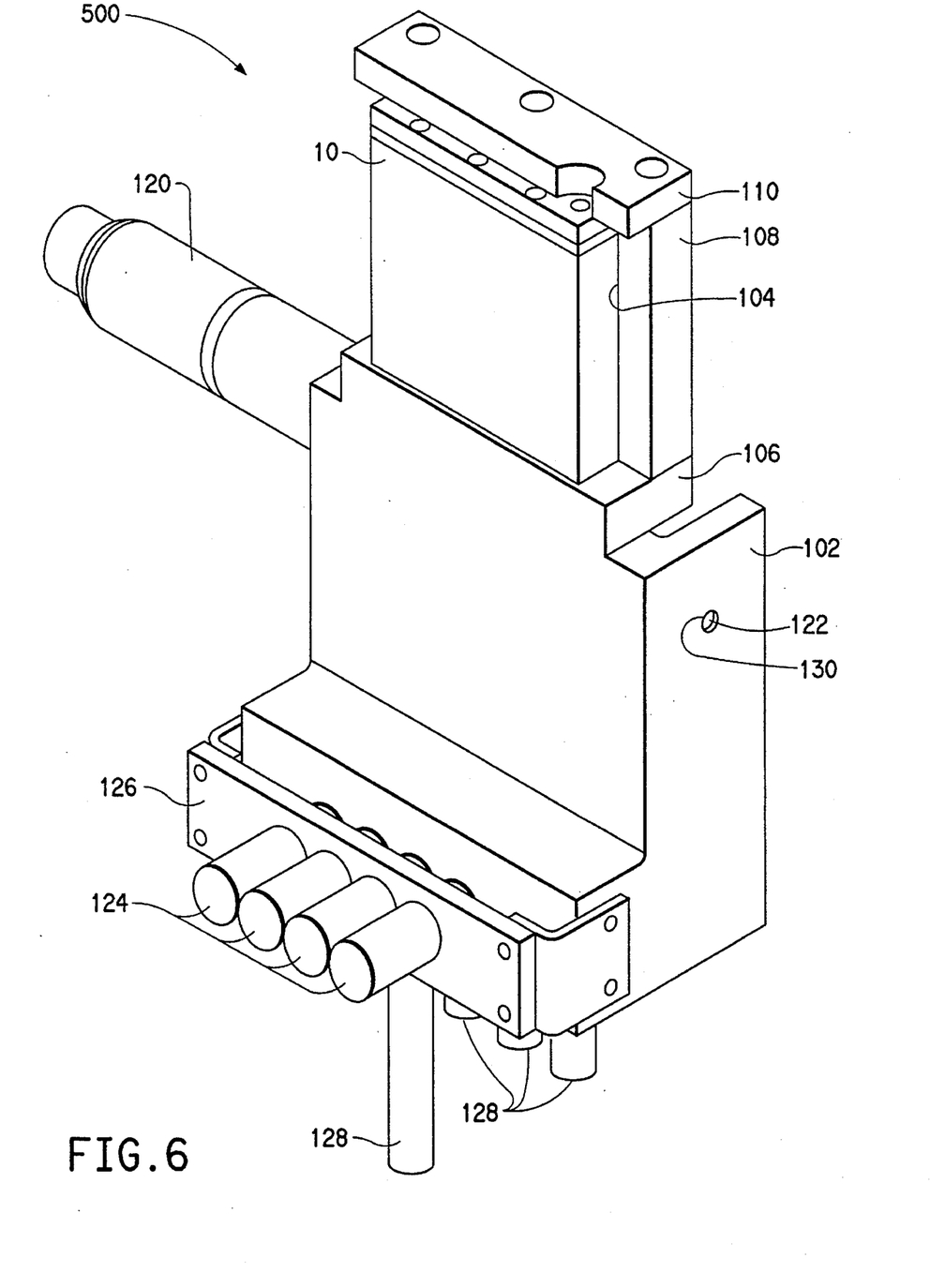
FIG. 6 is a schematic view of the actuating mechanism in the apparatus of FIG. 5.

Apparatus 10, as seen in FIGS. 1 and 2, is set up for 2-phase, 3-stage "top" separation and is made up of body 12; end 14; sliding bottoms 16, 18, 20, and 22, respectively operating in chambers 24, 26, 28, and 30; three ferromagnetic, mixing balls 32, one each in chambers, 24, 26, 28; luer fitting 48; and membrane seal 34. The sliding bottoms in the separation chambers 24, 26, 28 are each operated by rods 36, 38, and 40 (part of actuating apparatus 100, shown in cavity 104 or actuating apparatus 500 shown in FIG. 6) which controls the motion and position of the rods in the direction of the arrows. Each has a respective inlet 44 and outlet 46 in end 14. Inlet 44 of chamber 24 is supplied with luer fitting 48 which has a cap 34 sealing it except during loading with a syringe. Outlet 46' of chamber 30 is larger than the others and supplied with a plug 146, which closes it except during unloading with a pipette, sampling with an inoculating loop, or the like. Membrane seal 34 is bonded to cap 14 in such a manner that there are passages: from outlet 46 of chamber 24 to inlet 44 of chamber 26; from outlet 46 of chamber 26 to inlet 44 of chamber 28; and from outlet 46 of chamber 28 to inlet 44 of chamber 30 with each such passage covered by the taut membrane seal 34 which acts as a complete seal when pressed by isolation cap 140 and as a fairly good seal by virtue of that tautness except when a significant pressure is exerted in one of the chambers below. Each of chambers, 24, 26, 28 is stepped, at 24', 26', and 28' to limit the motion of the sliding bottoms. We prefer to accomplish this by having the lower portion of these chambers circular in cross-section with the upper portion oval which provides the needed step but allows the mixing ball to freely pass. A longer stroke requiring no step is provided for chamber 30 because no mixing is done here. Sliding bottom 22 is only pushed down when chamber 30 is loaded from chamber 28 at the appropriate time in the cycle. Chamber 30 is unloaded with a pipette or sampled with an inoculating loop through its unplugged outlet 46'.

In preparation for use, membrane seal 34 is bonded to end 14 preferably by heat-sealing bonding. The shape of the bonding tool is contoured to seal around the required passages described above as well as around the perimeter. All parts of the assembly are then sterilized preferably by gamma rays. Body 12 is then held so that face 52 is down and chambers, 24, 26, and 28 are loaded with a 2-phase solution. (Note: the composition of the two-phase solution put into chamber 24 may be different than that put into chambers 26 and 28 to account for the nature of the sample delivered, and its volume. Applicants also envision that the separation medium of all three chambers could be varied in relative concentrations and volumes to optimize the separation parameters particularly desired.) Balls 32 and sliding bottoms 16, 18, and 20 are inserted in chambers 24, 26, 28 approximately in the position shown in the figure and sliding bottom 22 is located in chamber 30, fully inserted also as shown. This latter is used to receive the separated fraction at the appropriate time in the process and to store the treated effluent until it is convenient to analyze the separated material. This requires no mixing ball.

For shipment, a isolation cap 140 as seen in FIG. 1 is snapped over face 52. The face of isolation cap 140 that mates with face 52 of body 12 is contoured to insure that pressure is applied through membrane seal 34 so that all outlets and inlets 46, 44 are held closed. Isolation cap 140 snapped into place. Chamber 24 is filled with 4 mL of two-phase solution. Chambers 26 and 28 are filled with only 3 mL of solution. This is done while consumable 10 is inverted with liquid injected up to the step 24', 26', 28'. Sliding bottoms 16, 18, 20 and 22 are inserted to the positions shown in FIG. 2 with sliding bottoms 16, 18, and 20 up against stops 24'. Means to bleed air from between the sliding bottom and the liquid must be provided. One way to accomplish this is by inserting a small-in-diameter but stout capillary tube between the wall and the sliding bottom which is possible because the sliding bottom is elastomeric. When the capillary is withdrawn, the elastomer expands to seal in the liquid with virtually no air. The sliding bottoms are held in position by friction. The consumable 10 is inverted. The cap 140 also features a molded on arrow, or other indicia, 142 to indicate the starting end to an operator and a cover 144 to hold plug 104 in place.

Figure 4:
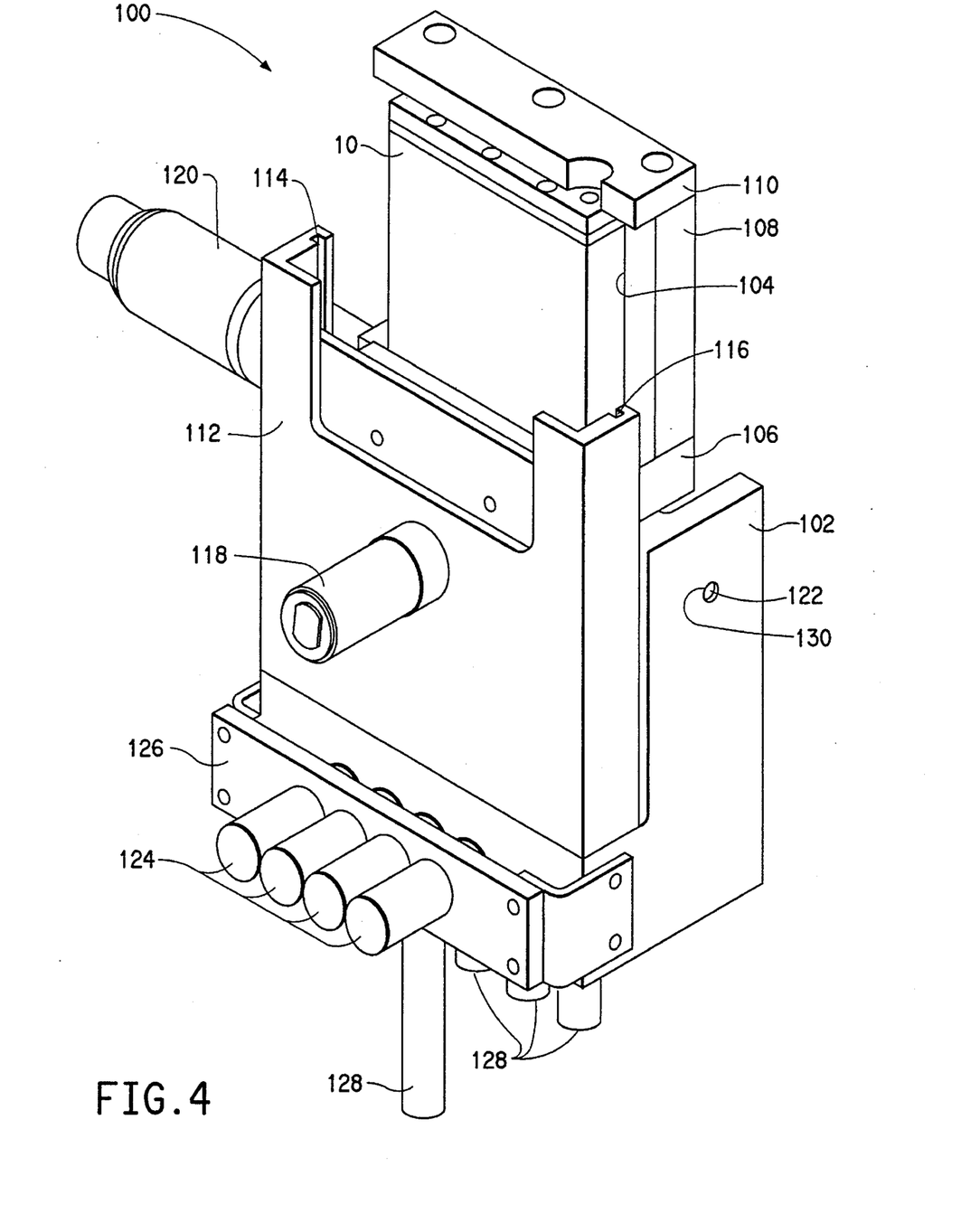
FIG. 4 is a perspective view of actuating apparatus for magnetic mixing and processing shown in position for top phase processing.
Figures 7, 8:
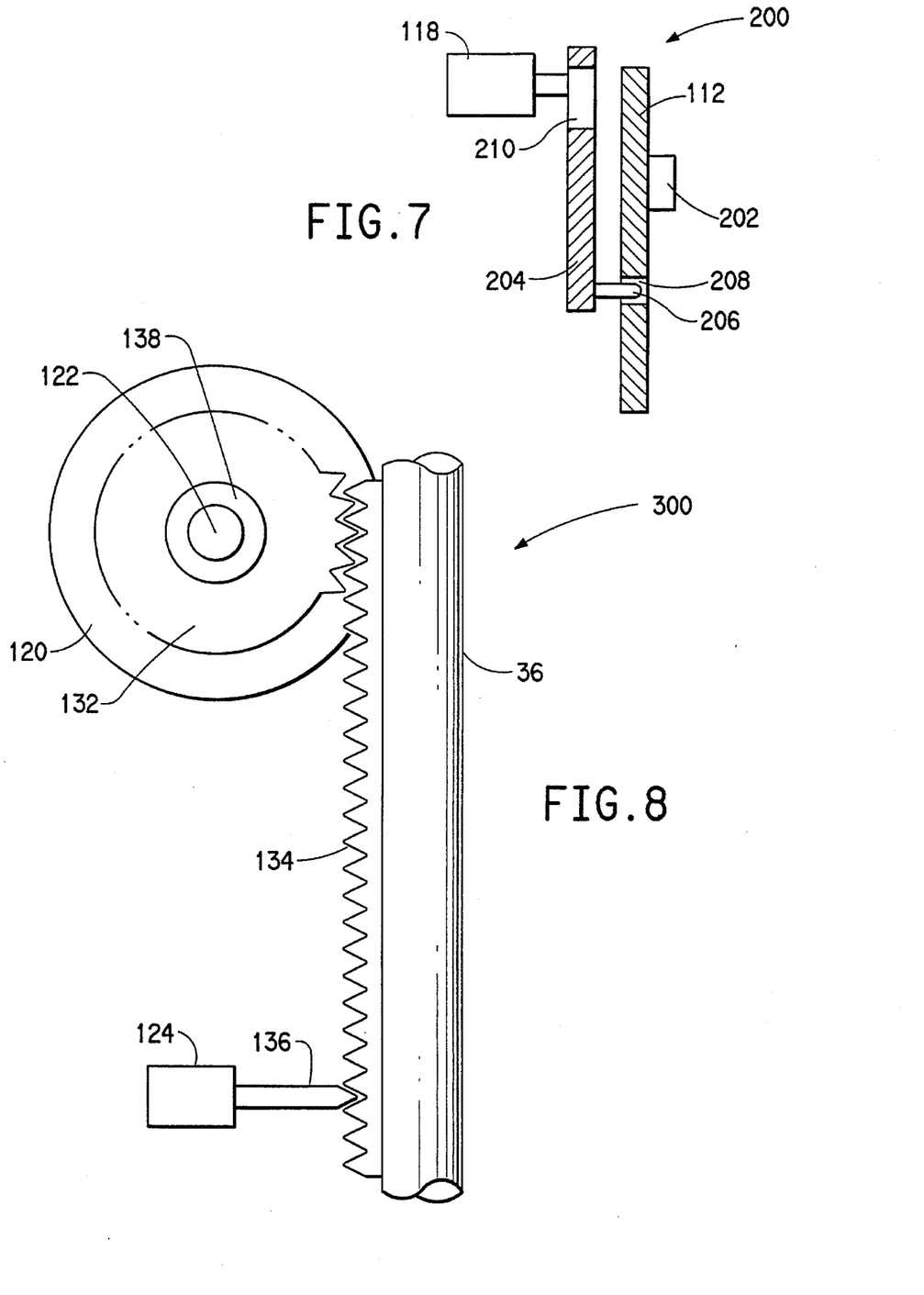
FIG. 7 is a side elevational view of the mixing mechanism used.
FIG. 8 is a side elevational view of the rod drive mechanism used.

FIG. 4 shows an actuating apparatus 100 for processing consumable 10 which combines the mixing and staging steps. This apparatus has a body 102 and a pocket 104 made up of platform 106, back 108 and overhanging top 110. There is a vertically reciprocable mixer slide 112 which is disposed in grooves 114, 116 and can be driven by motor 118 through a mechanism 200 shown in FIG. 7. Slide 112 carries permanent magnets 202, one for each chamber 24, 26, 28. Motor 118, through eccentric 210, scotch link 204 and drive pin 206, nested in slot 208, drives slide 112 which is constrained to move vertically by grooves 114, 116. Magnets 202 reciprocate in proximity to balls 32, which are thus magnetically coupled and reciprocate, to mix the contents of the chamber in which they are located.

Figure 10:
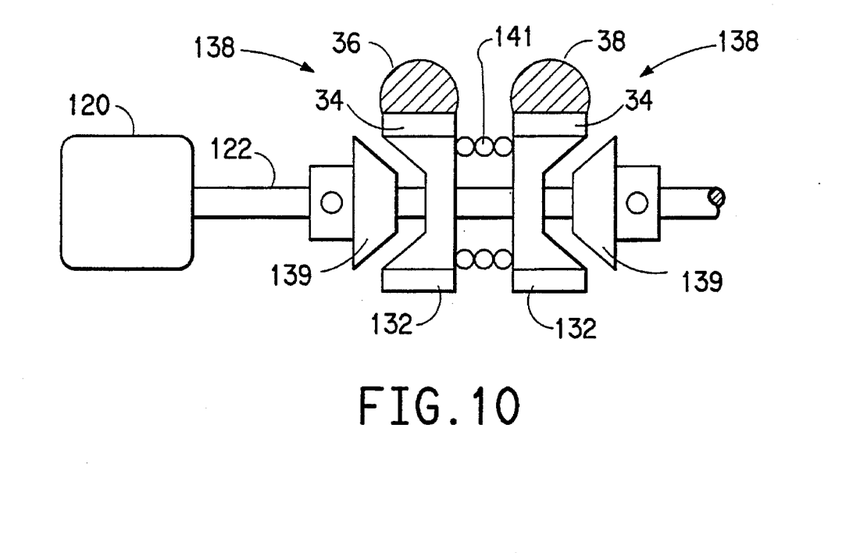
FIG. 10 is a side elevational view of a clutch mechanism used in the actuating apparatus of FIG. 6.

The part of apparatus 100 for operating the three stage, two phase, separation comprises motor 120, the shaft 122 which extends through body 102 and is rotatably supported in hole 130, four solenoids 124 mounted on bracket 126, and four covers 128 for rods 36, 38, 40, and 42. The mechanism 300 by which these components work is shown in detail in FIG. 8 which illustrates the configuration of one rod (here arbitrarily selected as rod 36). Reversible motor 120 drives shaft 122 on which four slip clutches 138 are mounted. Clutches made according to FIG. 10 are used. Each such clutch 138 carries a gear 132, rotatably and slideably mounted on shaft 122, in mesh with rack 134 which is mounted on rod 36. Cone member 139 is pinned or otherwise fixed to shaft 122. Spring 141 biases gears 132 against a cone member 139 there being one such spring between a pair of gears. Geometry and spring constant are selected to provide adequate driving force with suitable slippage when needed as is known. To facilitate this, we employ steel gears 132 engaging nylon cone members 139. Solenoids 124 controllably extend and retract plungers 136 to mesh or unmesh with racks 134. In operation, motor 120 is actuated with a rotation selected to drive any rod selected either up or down as the processing protocol may require. All four clutches 138 are driven in that selected rotation. The solenoid 124 for the rod 36, 38, 40 or 42 as the case may be which it is desired to drive is de-energized so that its plunger 136 is withdrawn from engagement with rack 134 permitting the rack to be driven in the selected direction up or down. The other solenoids 124 remain energized locking the particular rods in place, that is to say braking the particular sliding bottom(s). The clutches 138 associated with these rods continue to rotate but slip.

Figure 13:
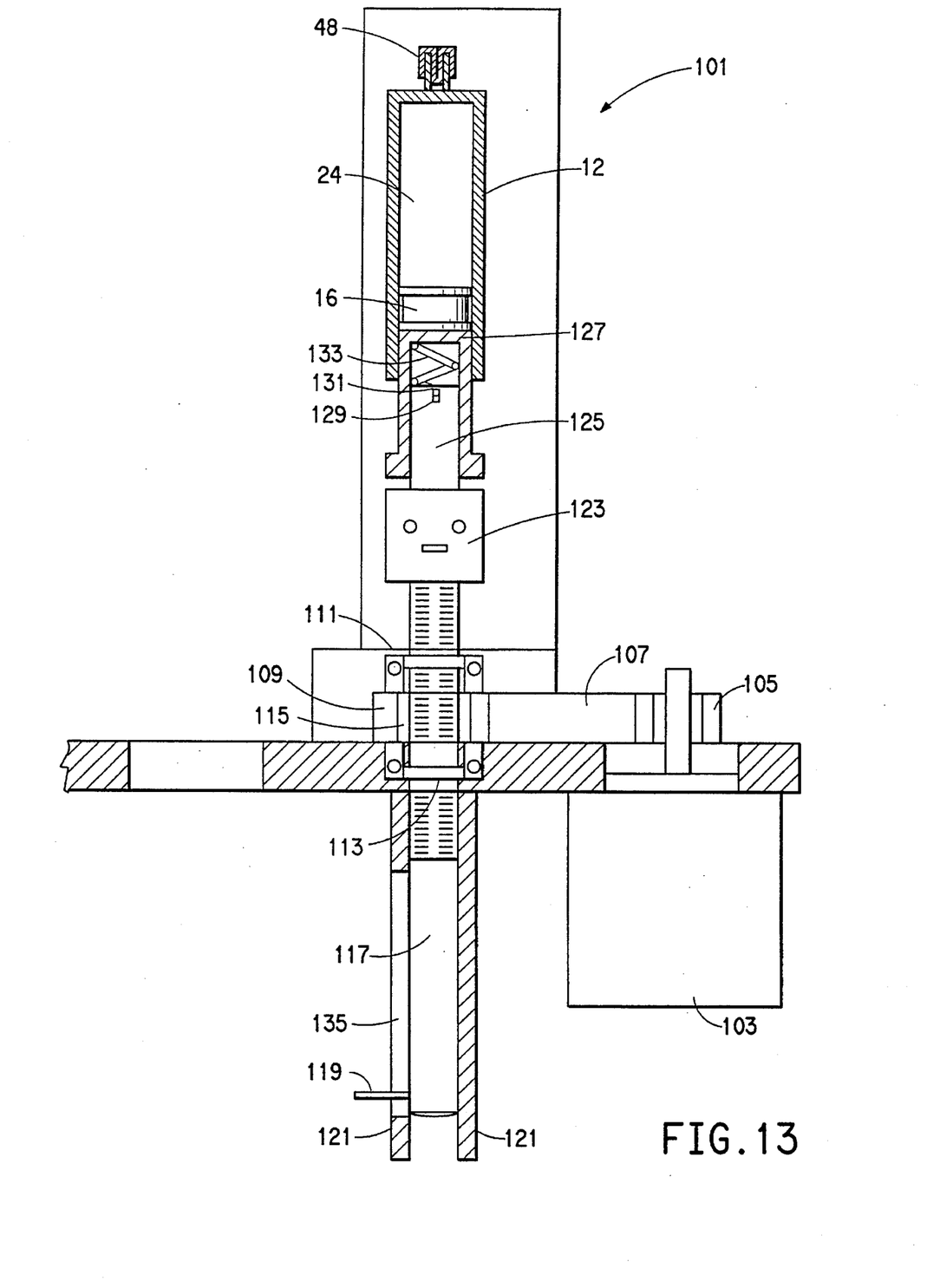
FIG. 13 is an elevational view in partial cross-section of a preferred embodiment for rod drive in an actuating apparatus.

An equivalent system can employ a screw mechanism driven by a reversible motor for each of rods 36, 38, 40, 42. This is shown in FIG. 13. The actuating apparatus is indicated by 101 and differs from that shown in FIG. 4 by the means to drive the rods. Motor 103, a reversible motor under the control of a preprogrammed personal computer or the like, drives timing gear 105, timing belt 107 and timing gear 109 which turns on stub shafts 115 in bearings 111, 113. A reversible stepping motor can be used. Nut 115 is integral with the inside of timing gear 109 and carries in threaded relationship rod 117. This is held against rotation by pin 119 which locks it to plates 121, part of device 101, and so it moves linearly as nut 115 rotates. Threaded rod 117 translate member 123 which moves inner shaft 125 which is an integral part of member 123 and is in internal sliding fit with outer shaft 127 which moves (in the upward direction as shown) a sliding bottom, here indicated 16 for convenience as typical. We prefer to use an acme thread for nut 115 and threaded rod 117. Thus the combination of inner/outer shafts 125/127 are the equivalents of rods discussed previously such as 36. The inner and outer shafts 125, 127 are interconnected by pin 129 in slot 131 and held apart by compression spring 133. This latter is selected to allow pin 129 to move to the other extreme in slot 131 when the loading between the inner and outer shafts exceeds a predetermined force which depends upon the material of construction used. For example, for a polyester body 12 we calculate a safe limit to be about 15 pounds. A sensor, not shown, on member 123 can thus signal an overload that might damage body 12 by excessive internal pressure. The signal from such a sensor can be used to shut down translation before damage is done. A sensor, also not shown, can be placed to detect pin at its lowest point of travel in slot 135 as a "home" position. Counting of steps from this position can indicate full stroke action and detect any time at which motion upwards was stopped by a premature overload condition.

In use, according to one preferred protocol, the procedure for inoculation and loading using the consumable of the invention packed in a pouch in kit form with an inoculating tip and loaded with the appropriate two-phase medium in the first three chambers as described above is as follows:

Provide sterile inoculating syringe.

Attach the tip provided to the syringe.

Draw 1 ml sample from sample container using syringe fitted with tip.

Remove and discard the tip.

Uncover luer fitting.

Attach syringe to consumable at luer fitting & inject the sample into chamber 1.

Remove syringe and attach cap to luer fitting.

Remove the locking cap to open the fluid ports.

Orient the consumable and the actuating instrument facing up or down, and load the consumable into the actuating instrument.

Start the instrument.

Once the consumable is in the instrument and it is started, the instrument will manipulate it as needed under the control of a computer or the like using a preselected program to execute the process. The sequence of Mix, Settle, and transfer is repeated through stages 1, 2, & 3. Finally, the instrument transfers a small volume from Chamber 3 to Chamber 4 (about 1 mL). At this point the instrument has finished, and it may beep, for example, to indicate such to operator. The operator will then remove the plastic plug covering the access port and draw off the sample using a pipette, for example, by inserting a streaking loop through the port. The sample may then be analyzed, for example, by streaking onto plates or by innoculating into growth medium.

Figure 5:
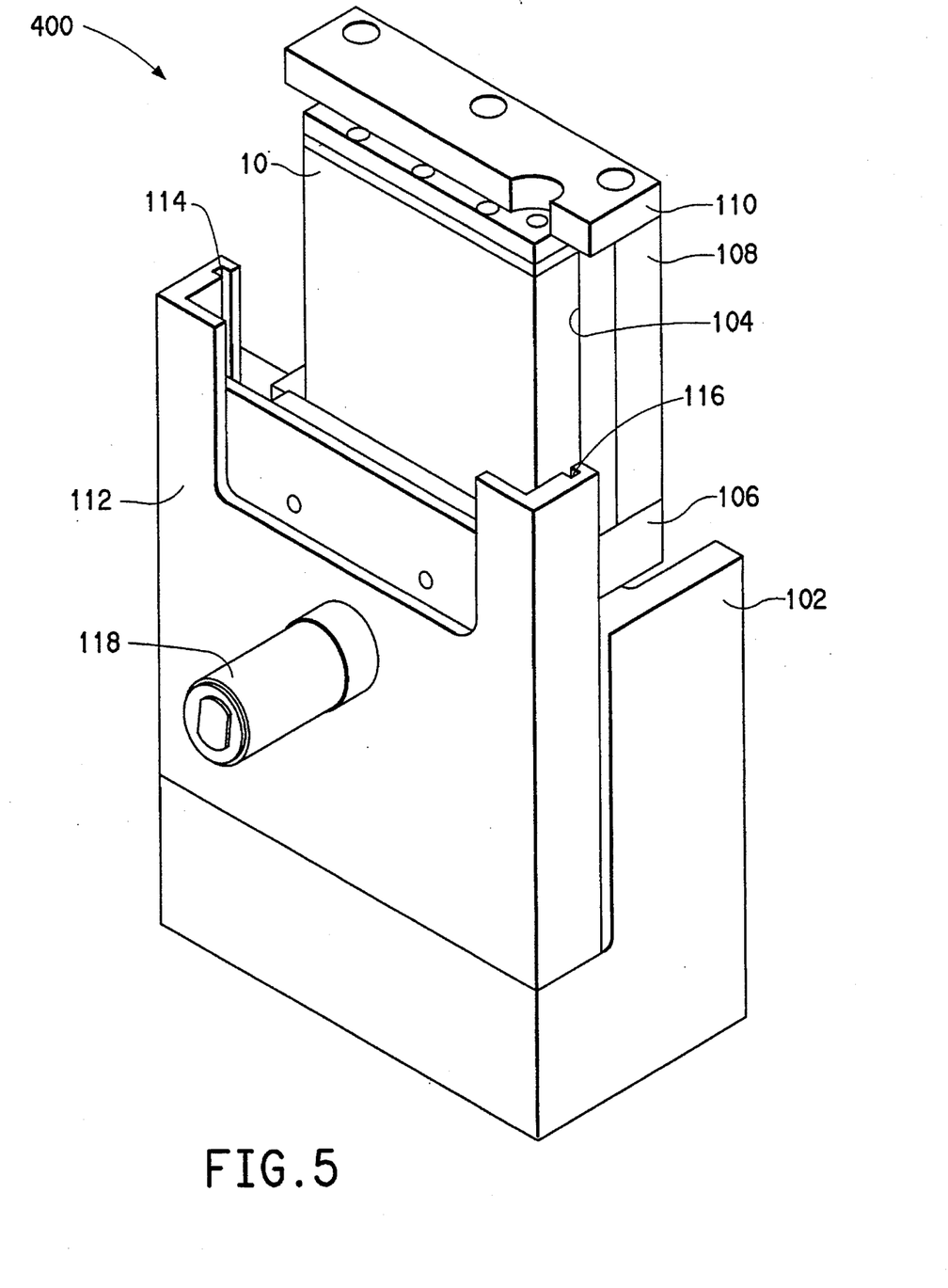
FIG. 5 is a schematic elevational view in cross-section of the mechanism for magnetic mixing in the apparatus of FIG. 4.

To this point the procedure has been described using the apparatus of FIG. 4. Because the mixing time is a small percentage of the processing time, for automated or semi-automated operation we prefer using the apparatus 400 shown in FIG. 5 for stand-alone mixing and the apparatus 500 of FIG. 6 for processing. As the numbering indicates, the devices functionally are the same as their counterparts in the functionally combined apparatus of FIG. 4.

It is recognized that certain target microbes or other desired sample material may be separated into the bottom phase. To process these samples, consumable 10 is supplied with the appropriate two-phase media. It is charged with sample fluid as described and inverted before being placed in the selected process apparatus which itself has been inverted. The stands and details of mounting are not shown in the drawings. For example, the apparatus of FIG. 4 is rotatably mounted on a stand with a rotary joint approximately at the level of motor 118 fixed to its back which rotates about an axis parallel to the axis of motor 118. Operation is exactly as above with the exception of the orientation. It will be recognized that a consumable 10 in any of apparatus 100, 400, or 500 installed so that the open ends of chambers 24, 26, 28, 30 are up, and sliding bottoms 16, 18, 20, and 22 are operated from the top down, will transfer the bottom phase.

If a sample contains two microbes, for example, one favoring the top and the other the bottom phase, then the kit of necessity includes a consumable 10 for each mode of operation and both must be run. It is contemplated that these consumables 10 will be identified and, optionally, they may be keyed to the actuating apparatus according to its orientation.

Figure 9:
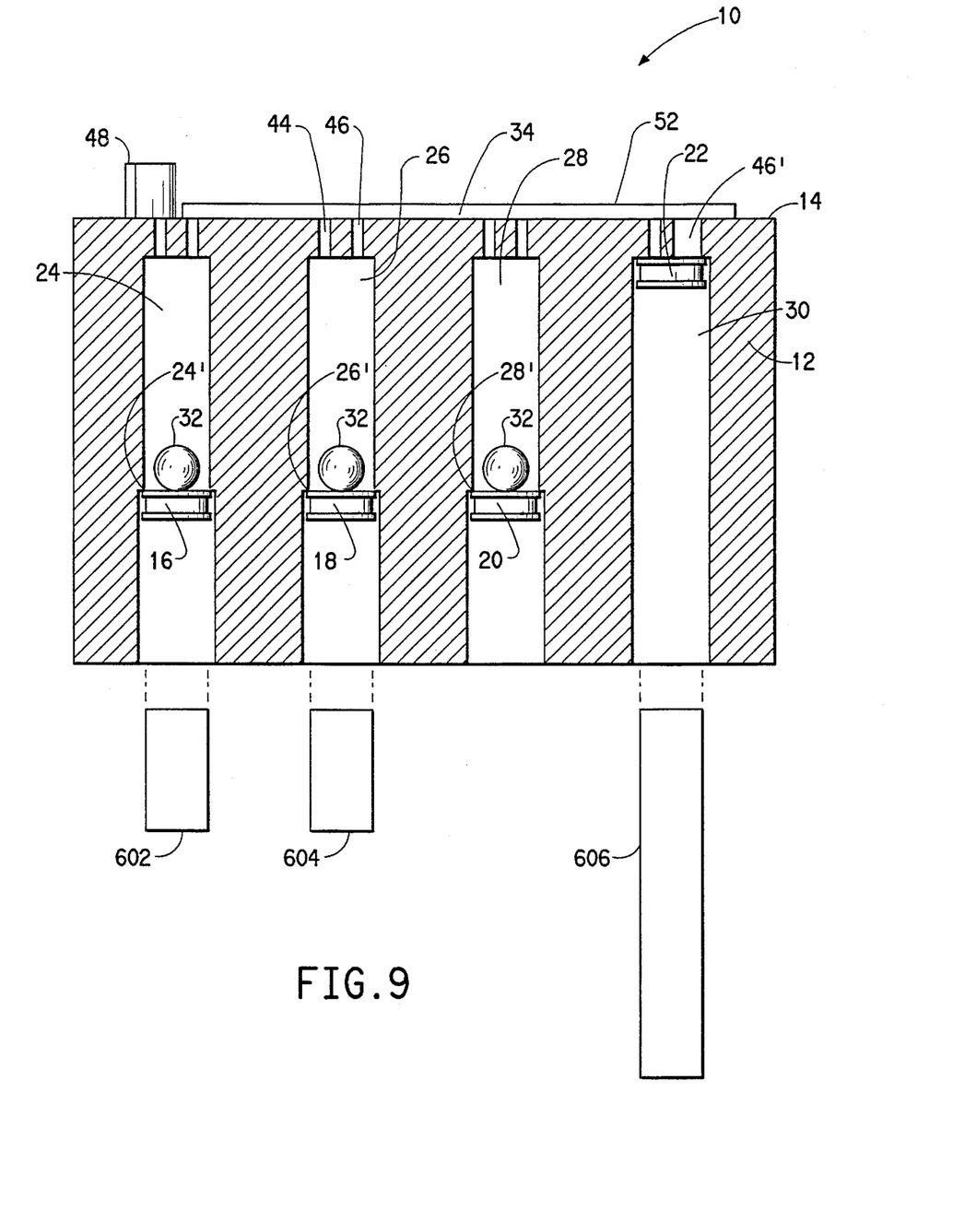
FIG. 9 is a schematic cross-section of a method and apparatus for hand operation of the invention.

In an other protocol, consumable 10 may be hand operated with appropriate tools as shown in FIG. 9 as shown in FIG. 9 and described below. The tooling comprises three rods 602, 604, 608 whose diameters permit easy insertion into the lower shafts of the chambers (24, 26, 28, 30). The length of two of the rods 602, 604 permits them to extend from the underside of sliding bottoms 16, 18, and 20 when they are up against steps 24', 26', 28' respectively to about 1 cm outside body 12. Rod 608 is longer and extends the same amount outside from the underside of sliding bottom 22 when it is fully inserted in chamber 30. The rods may be attachable to the sliding bottoms as by a threaded fastener if so desired.

In use, rods 602, 604 and 606 are inserted into body 12 of the consumable 10 to contact and brake sliding bottoms 18, 20 and 22, the appropriate two-phase aqueous medium having been inserted previously in chambers 25, 26, and 28 as described elsewhere. Body 12 is held in the hand with a finger locking each of the rods in place. With a hypodermic syringe, the charge carrying the material to be separated is injected into chamber 24 driving bottom 16 down to accommodate the added volume of fluid (ordinarily 1 mL). Ball 32 is reciprocated by passing a magnet back and forth on the outside of the chamber to mix the contents. The assembly then is allowed to stand until separation takes place (usually 30 minutes). Luer 48 is capped and fluid is transferred from chamber 24 to chamber 26. This is done by inserting long rod 606 into chamber 30 and a short rod into chamber 28 and pushing sliding bottom 16 to step 24' (with any convenient rod-like tool, not shown) to transfer the selected, separated fraction into chamber 26 in a volume equal to that originally injected into chamber 24 driving sliding bottom 18 down. Flow of fluid into chambers 28 or 30 is prevented because the long and short rods, each held by a finger, brakes the selected bottoms against sliding. Ball 32 is reciprocated by passing a magnet back and forth on the outside of the chamber to mix the contents. Separation is repeated and transfer is made, this time with a short braking rod in chamber 24 (to prevent reverse flow) and the long rod 606 in chamber 30 to provide the brake there. Mixing and separation is repeated for the third time and transfer made to chamber 30 with no rod in chamber 30, the holding chamber, permitting sliding bottom 22 to be driven down while finger-held short rods provides brakes in chambers 24 and 26. Chamber 30 is sampled when convenient through port 46'. Note that this procedure is the same for a separation series in which the top fraction is of interest or one in which the bottom fraction is of interest. The only difference is in which end of consumable 10 is up during the process.

A simple jig 700 to hold consumable 10 during the above steps can be made if desired. See FIG. 11. A "C-shaped" structure 702 is used which has upper and lower extensions 704 and 706 respectively with a vertical wall 728 in between.

Figure 11:
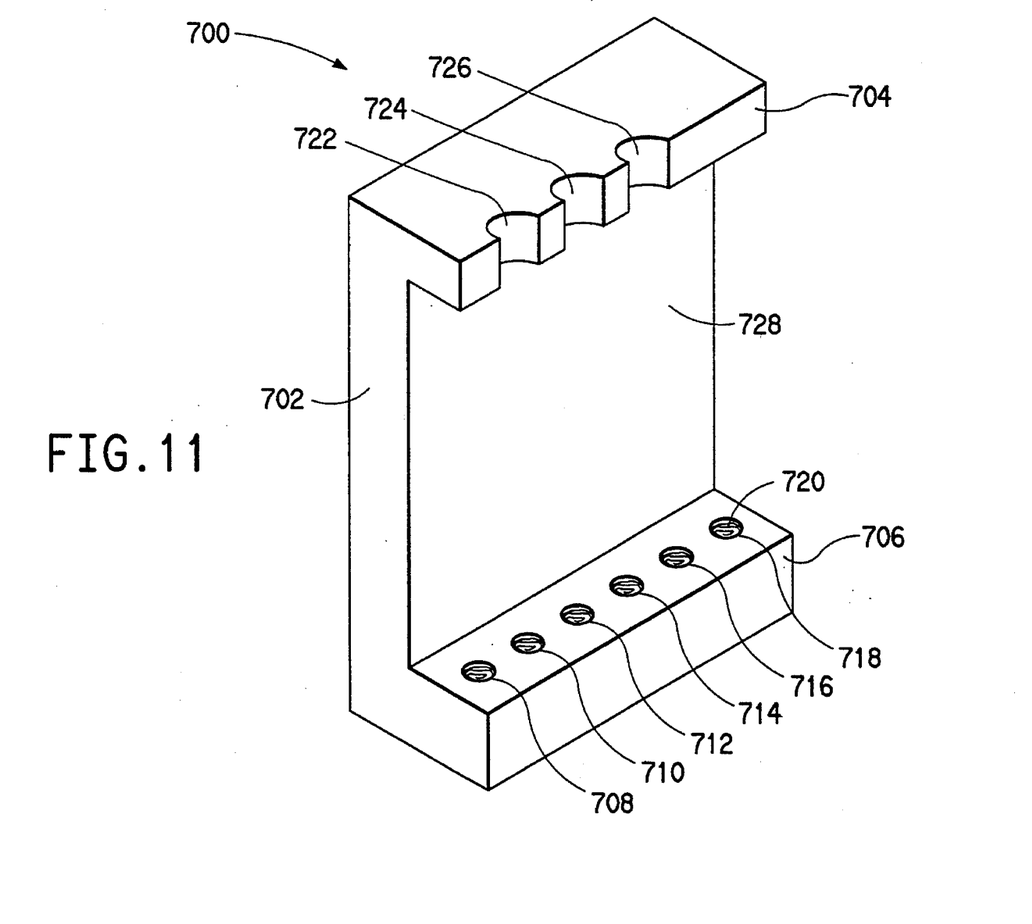
FIG. 11 is a perspective view of further apparatus for hand operation of the invention comprising a holding jig.

The lower extension 706 has six vertical holes, 708, 710, 712, 714, 716, and 718. Hole 712 is a through hole. The others are blind holes each of which contains a captive spring 720. In the upper extension 704 there are three semi-circular reliefs 722, 724 and 726. These are on axis with holes 708, 710, and 712 respectively and are sized to clear luer 48 when a consumable is in place abutting wall 728.

In use, the procedure is the same as that just recited except that the consumable 10 is held in jig 700 instead of in the hand. For initial inoculation, luer 48 is placed in relief 726. The first transfer is done in the same position. For the second transfer, luer 48 is put into relief 724. For the third transfer, relief 722 is used. When chamber 30 is to be sampled, consumable 10 is inserted into jig 700 so that luer 48 is beyond body 702 and chamber 30 and port 46' are aligned with relief 726.

Figure 12:
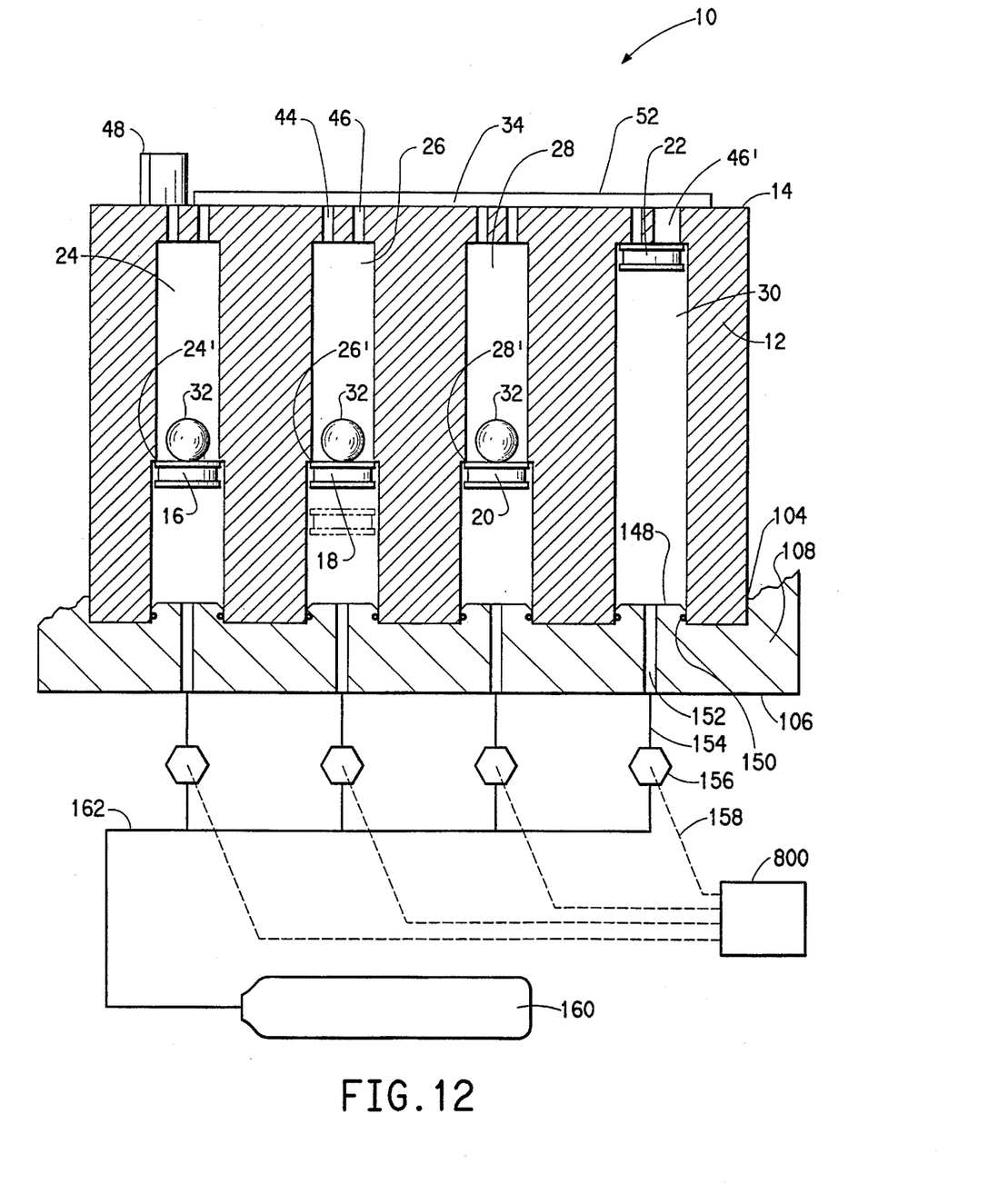
FIG. 12 is a schematic view of the apparatus of the invention in actuating apparatus which is fluid driven.

Refer now to FIG. 12. In this drawing is seen apparatus in which actuation is carried out by fluid power unlike the embodiments discussed above in which rods, actuated mechanically or electromechanically, move and/or brake the sliding bottoms 16, 18, 20, 22 using rods 602, 604, and 606. In this Figure, a consumable 10 (in cross-section) is seen inserted into the cavity 104 of a modified actuating apparatus 100 in which the means to move, and to prevent moving, the sliding bottoms is fluidic, preferably compressed air. Platform 106 has a protuberance 148 for each chamber (24, 26, 28, 30) with a means to insure a good fluid seal such as o-ring 150. Each of the chambers has a passage 152 that is connected by tubing 154 to and electrically controlled valve 156 which received electrical signals from control device 800 by cables 158. Each valve 156 is in fluid connection with a source of fluid power 160 by way of tubing 162.

Consider one typical operation. Assume that a partially separated sample is in chamber 26. Sliding bottom 18 would be at a position shown by the broken lines. After mixing and settlement as described previously, the protocol calls for a transfer to chamber 28. Controller 800 would open valves 156 that supply air to chambers 24, 28 and 30 locking bottom 16 against stop 24', bottom 20 against stop 28', and bottom 22 at the top of chamber 30. Then the valve connected to chamber 26 would be opened and air would force bottom 18 up to stop 26' driving the selected volume of fluid into chamber 28 moving bottom 20 down the necessary distance which is permitted by using valves that vent to atmosphere in the off position.

We claim:

1. Apparatus for performing multi-phase liquid separation comprising:

a separation chamber which has an open end and a closed end, said closed chamber end having an inlet passage and an outlet passage;

a sliding bottom inserted into the open end of said separation chamber for sliding motion therein while providing a liquid seal thereto;

means disposed within said separation chamber for mixing liquid within said separation chamber;

removable inlet closing means;

removable outlet closing means; and means for moving in a selected stroke said sliding bottom toward said closed end and means for selectively preventing said sliding bottom from being moved toward said open end along said stroke at any selected location between said open end and said closed end.

2. The apparatus of claim 1 wherein said separation chamber is charged with a selected volume of two-phase aqueous medium completely filling said chamber between said closed end and said sliding bottom.

3. The apparatus of claim 1 wherein said mixing means is a magnetically-responsive ball disposed in said chamber between said closed end and said sliding bottom.

4. The apparatus of claim 1 wherein said means to move and prevent moving of said sliding bottom is a rod of selected length and diameter to freely enter said chamber through said open end to contact said sliding bottom and selectively move said sliding bottom toward said closed end or selectively hold said sliding bottom against sliding toward said open end by manual or mechanized translation or braking of said rod.

5. The apparatus of claim 1 wherein said means for selectively moving and preventing said sliding bottom from being moved comprises:

sealing means to seal said open end of said chamber;

a source of fluid power;

a valve for said chamber in fluid communication with said source and said chamber through said sealing means; and means to selectively open and close said valves in selected sequence.

6. The apparatus of claim 1 wherein the internal portion of said chamber wherein said sliding bottom slides is a cylinder.

7. The apparatus of claim 6 wherein said chamber has stop means limiting the motion of said sliding bottom toward said closed end.

8. The apparatus of claim 7 wherein the internal portion of said chamber between said closed end and the internal portion wherein said sliding bottom slides is oval, the intersection of the two portions thereby providing said stop means.

9. The apparatus of claim 1 further comprising:

a storage chamber which has an open end and a closed end, said closed end having an inlet passage and an outlet passage, said storage chamber and said closed and open ends thereof being adjacent to said separation chamber and said open and closed ends thereof, the outlet passage of said separation chamber interconnected by a transfer passage to the inlet passage of said storage chamber;

a sliding bottom inserted into the open end of said storage chamber for sliding motion therein while providing a liquid seal thereto;

means for selectively moving said sliding bottom in said storage chamber toward said closed end and selectively preventing said sliding bottom from being moved toward said open end.

10. The apparatus of claim 9 wherein said separation chamber is charged with a selected volume of two-phase aqueous medium.

11. The apparatus of claim 9 wherein said mixing means is a magnetically-responsive ball disposed in said separation chamber between said closed end and said sliding bottom.

12. The apparatus of claim 9 wherein said means to move and prevent moving of said sliding bottoms are rods of selected length and diameter to freely enter said chambers through said open ends to contact said sliding bottoms and selectively move said sliding bottoms towards said closed ends or selectively hold said sliding bottoms against sliding toward said open ends by manual or mechanized translation or braking of said rods.

13. The apparatus of claim 12 comprising mechanized translation and braking effected by a threaded translating rod driven by an internal nut rotated by a reversible electric stepping motor.

14. The apparatus of claim 9 wherein said means for selectively moving and preventing said sliding bottom from being moved comprises:

means to seal said open ends of each said chamber;

a source of fluid power;

a valve for each said chamber in fluid communication with said source and said chamber through said sealing means; and means to selectively to open and close said valves in selected sequence.

15. The apparatus of claim 9 wherein said transfer passage is a region extending between said outlet passage of said separation chamber and said inlet passage of said storage chamber and said region is covered with a thin film sealed peripherally around said outlet passage thereof, said region and said inlet passage thereof.

16. The apparatus of claim 15 wherein said thin film is pressed by a pad fixed to a cover removably fastened to said closed ends to close each of said passages during shipping and handling.

17. The apparatus of claim 9 wherein said transfer passage is a groove extending between said outlet passage of said separation chamber and said inlet passage of said storage chamber and said groove is covered with a thin film sealed peripherally around said outlet passage thereof, said groove, and said inlet passage thereof.

18. The apparatus of claim 17 wherein said thin film is pressed by a pad fixed to a cover removably fastened to said closed ends to close each of said passages during shipping and handling.

19. The apparatus of claim 18 wherein said means for selectively moving and preventing moving each of said sliding bottoms are rods of selected length and diameter to freely enter said chambers through said open ends to contact said sliding bottoms and selectively move said sliding bottoms towards said closed ends or selectively hold said sliding bottoms against sliding toward said open ends by manual or mechanized translation or braking means.

20. The apparatus of claim 19 wherein the mixing means comprise a magnetically-responsive ball disposed in each of said separation chambers between said closed ends and said sliding bottoms.

21. The apparatus of claim 20 wherein said separation chambers are charged with selected volumes of two-phase aqueous medium completely filling said chambers between said closed ends and said sliding bottoms and a volume of a liquid sample containing organic matter to be separated is inoculated into said first separation chamber displacing the sliding bottom therein to accommodate said added volume in combination with mixing apparatus comprising:

a cavity for holding said apparatus of claim 20;

a permanent magnet; and means to reciprocate said magnet in proximity to said magnetically responsive balls.

22. The apparatus of claim 20 wherein said separation chambers are charged with selected volumes of two-phase aqueous medium completely filling said chambers between said closed ends and said sliding bottoms and a volume of a liquid sample containing organic matter to be separated is inoculated into said first separation chamber displacing the sliding bottom therein to accommodate said added volume in combination with actuating apparatus comprising:

a holding cavity; and means to selectively translate or brake said rods;

whereby an aliquot portion of said sample-containing medium is selectively transferred sequentially from chamber to chamber without reverse flow or unselected overflow to a subsequent chamber; and said actuating apparatus is selectively disposed relative to gravity such that said aliquot portion is either a top or bottom phase.

23. The apparatus of claim 20 wherein said separation chambers are charged with selected volumes of two-phase aqueous medium completely filling said chambers between said closed ends and said sliding bottoms and a volume of a liquid sample containing organic material to be separated is inoculated into said first separation chamber displacing the sliding bottom therein to accommodate said added volume in combination with mixing and actuating apparatus comprising:

a holding cavity;

means to selectively translate or brake said rods whereby an aliquot portion of said sample-containing medium is transferred sequentially from chamber to chamber without reverse flow or unselected overflow to a subsequent chamber;

a permanent magnet;

means to reciprocate said magnet in proximity to said magnetically-responsive balls; and wherein said actuating apparatus is selectively disposed relative to gravity such that said aliquot portion is either a top or bottom phase.

24. The apparatus of claim 19 comprising mechanized translation and braking effected by a threaded translating rod driven by an internal nut rotated by a reversible electric stepping motor.

25. The apparatus of claim 9 wherein each said sliding bottom is a cylinder.

26. The apparatus of claim 25 wherein said separation chamber has stop means limiting the motion of said sliding bottom toward said closed end thereof.

27. The apparatus of claim 26 wherein the internal portion of said separation chamber between the closed end and the portion wherein said sliding bottom slides is oval, the intersection of the two portions thereby providing said stop means.

28. The apparatus of claim 9 for performing two-phase aqueous separation wherein:

there is a plurality of separation chambers disposed in sequential, side-by-side relationship and the outlet passage of a first of said plurality of chambers interconnected by a transfer passage to a further one of said separation chambers and so on in sequentia, the outlet passage of the last of said plurality of separation chambers being interconnected by a transfer passage to the inlet passage of said storage chamber.

29. The apparatus of claim 28 wherein said separation chambers are charged with selected volumes of two-phase aqueous medium completely filling said chambers between said closed ends and said sliding bottoms.

30. The apparatus of claim 28 wherein the mixing means comprise a magnetically-responsive ball disposed in each of said separation chambers between said closed ends and said sliding bottoms.

31. The apparatus of claim 28 wherein the internal portion of said chambers wherein said sliding bottoms slide is a cylinder.

32. The apparatus of claim 31 wherein said separation chambers have stop means limiting the motion of said sliding bottoms toward said closed ends.

33. The apparatus of claim 32 wherein the internal portion of said separation chambers between said closed ends and the portion wherein said sliding bottoms slide are oval, the intersection of the two portions thereby providing said stop means.

34. The apparatus of claim 28 wherein said transfer passages are a region extending between each of said outlet and inlet passages of said sequential chambers and said inlet passage of said storage chamber and said region is covered with a thin film sealed peripherally around said outlet passages thereof said region, and said inlet passages thereof.

35. The apparatus of claim 34 wherein said thin film is pressed by a pad fixed to a cover removably fastened to each of said closed ends to close said respective passages during shipping and handling.

36. The apparatus of claim 28 wherein said transfer passages are grooves extending between each of said outlet and inlet passages of said sequential chambers and said grooves are covered with a thin film sealed peripherally around each said individual outlet passages thereof, said grooves, and said inlet passages thereof.

37. The apparatus of claim 36 wherein said thin film is pressed by a pad fixed to a cover removably fastened to each of said closed ends to close said respective passages during shipping and handling.

38. The apparatus of claim 28 wherein said means for selectively moving and preventing said sliding bottoms from being moved comprise:

means to seal said open ends of each said chamber;

a source of fluid power;

a valve for each said chamber in fluid communication with said source and each said chamber through said sealing means; and means to selectively open and close said valves singly or in combination in selected sequence.

39. The apparatus of claim 38 wherein the mixing means is a magnetically-responsive ball disposed in each of said separation chambers between said closed ends and said sliding bottoms.

40. The apparatus of claim 39 wherein said separation chambers are charged with selected volumes of two-phase aqueous medium completely filling said chambers between said closed ends and said sliding bottoms and a volume of a liquid sample containing organic matter to be separated is inoculated into said first separation chamber displacing the sliding bottom therein to accommodate said added volume in combination with mixing apparatus comprising:

a holding cavity;

a permanent magnet; and means to reciprocate said magnet in proximity to said magnetically-responsive balls.

41. The apparatus of claim 39 wherein said separation chambers are charged with selected volumes of two-phase aqueous medium completely filling said chambers between said closed ends and said sliding bottoms and a volume of a liquid sample containing organic matter to be separated is inoculated into said first separation chamber displacing the sliding bottom therein to accommodate said added volume in combination with actuating apparatus comprising:

a holding cavity wherein said means to seal said open ends is incorporated in said cavity and whereby said means to selectively to open and close said valves singly or in combination in selected sequence is actuatable to transfer an aliquot portion of said sample-containing medium sequentially from chamber to chamber without reverse flow or unselected overflow to a subsequent chamber; and     said actuating apparatus is selectively disposed relative to gravity such that said aliquot portion is either a top or bottom phase.

42. The apparatus of claim 39 wherein said separation chambers are charged with selected volumes of two-phase aqueous medium completely filling said chambers between said closed ends and said sliding bottoms and a volume of a liquid sample containing organic material to be separated is inoculated into said first separation chamber displacing the sliding bottom therein to accommodate said added volume in combination with mixing and actuating apparatus comprising:

a permanent magnet;

means to reciprocate said magnet in proximity to said magnetically-responsive balls;

a holding cavity wherein said means to seal said open ends is incorporated and whereby said means to selectively to open and close said valves singly or in combination is selected sequence is actuatable to transfer an aliquot portion of said sample-containing medium sequentially from chamber to chamber without reverse flow or unselected overflow to a subsequent chamber; and     said actuating apparatus is selectively disposed relative to gravity such that said aliquot portion is either a top or bottom phase.

43. The apparatus of claim 28 wherein there are three separation chambers.

44. Apparatus for performing multi-phase liquid separation comprising:

a separation chamber which has an open end and a closed end, said closed chamber end having an inlet passage and an outlet passage;

a sliding bottom inserted into the open end of said separation chamber for sliding motion therein while providing a liquid seal thereto;

means for mixing liquid within said separation chamber;

removable inlet closing means;

removable outlet closing means; and means for moving in a selected stroke said sliding bottom toward said closed end and means for selectively preventing said sliding bottom from being moved toward said open end along said stroke at any selected location between said open end and said closed end, wherein said means for selectively moving and preventing said sliding bottom from being moved comprises:

sealing means to seal said open end of said chamber;

a source of fluid power;

a valve for said chamber in fluid communication with said source and said chamber through said sealing means; and     means to selectively open and close said valve in selected sequence.

45. Apparatus for performing multi-phase liquid separation comprising:

a separation chamber which has an open end and a closed end, said closed chamber end having an inlet passage and an outlet passage;

a sliding bottom inserted into the open end of said separation chamber for sliding motion therein while providing a liquid seal thereto;

means for mixing liquid within said separation chamber;

removable inlet closing means;

removable outlet closing means; and means for moving in a selected stroke said sliding bottom toward said closed end and means for selectively preventing said sliding bottom from being moved toward said open end along said stroke at any selected location between said open end and said closed end;

a storage chamber which has an open end and a closed end, said closed end having an inlet passage and an outlet passage, said storage chamber and said closed and open ends thereof being adjacent to said separation chamber and said open and closed ends thereof, the outlet passage of said separation chamber interconnected by a transfer passage to the inlet passage of said storage chamber;

a sliding bottom inserted into the open end of said storage chamber for sliding motion therein while providing a liquid seal thereto;

means for selectively moving said sliding bottom in said storage chamber toward said closed end and selectively preventing said sliding bottom from being moved toward said open end.

\* \* \* \* \*